United States Patent
Charters et al.

(10) Patent No.: US 6,541,045 B1
(45) Date of Patent: Apr. 1, 2003

(54) HERBAL COMPOSITION AND METHOD FOR COMBATING INFLAMMATION

(75) Inventors: Alec Charters, Salt Lake City, UT (US); James Selander, Park City, UT (US); Shayne Morris, Ogden, UT (US); Robert Charles Thompson, Peterson, UT (US); Lori Blackner, Chattanooga, TN (US)

(73) Assignee: Nutraceutical Corporation, Park City, UT (US)

( * ) Notice: Subject to any disclaimer, the term of this patent is extended or adjusted under 35 U.S.C. 154(b) by 0 days.

(21) Appl. No.: 10/035,203

(22) Filed: Jan. 4, 2002

(51) Int. Cl.[7] .......................... A61K 35/78; A01N 65/00
(52) U.S. Cl. ...................... 424/737; 424/725; 424/764; 424/766
(58) Field of Search ................. 424/725, 766, 424/764, 737

(56) References Cited

U.S. PATENT DOCUMENTS 5,989,556 A * 11/1999 Tsai et al. .................... 514/885
6,264,995 B1    7/2001 Newmark et al. .......... 424/725

OTHER PUBLICATIONS

Computer PROMT Abstract Gupta "The role of phytopharmaceuticals in topical pain relief" Household & Personal Products Industry (Dec. 2001) vol. 38. No. 12 pp 110 (7) Rodman Publications.*

* cited by examiner

Primary Examiner—Herbert J. Lilling
(74) Attorney, Agent, or Firm—Jagtiani + Guttag

(57) ABSTRACT

An herbal composition for combating inflammation, comprising therapeutically effective amounts of Japanese knotweed, Devil's claw, grapeskin, and syzygium is provided. Also provided is an herbal composition for treating a cough and/or common cold, comprising therapeutically effective amounts of Japanese knotweed, lobelia, echinacea, slippery elm, Devil's claw, adhatoda, vitamin C, grapeskin, and syzygium. An herbal composition for alleviating menstrual discomfort, comprising therapeutically effective amounts of Japanese knotweed, chaste tree berry, Mexican wild yam, dandelion, Devil's claw, grapeskin, and syzygium is provided. Also provided is an herbal composition for soothing muscles and joints, comprising therapeutically effective amounts of Japanese knotweed, N-acetyl D-glucosamine, chondroitin sulfate, D-glucosamine hydrochloride, methylsulfonylmethane, grapeskin, syzygium, and Devil's claw. Methods of using the herbal compositions are also provided.

66 Claims, 1 Drawing Sheet

HERBAL COMPOSITION AND METHOD FOR COMBATING INFLAMMATION

BACKGROUND OF THE INVENTION

1. Field of the Invention

The present invention relates generally to herbal compositions and methods for combating inflammation.

2. Description of the Prior Art

Arthritic disorders, including rheumatism, osteoarthritis, dysplasia, lupus, bursitis, and gout, are all characterized by inflammation and pain in bones, joints, muscles, and related connective tissues. Most of the forms are progressive. Those who suffer from inflammation experience pain and discomfort and may, in advanced cases, lose the effective use of inflamed joints. Thus, the goal of therapeutic methods for treating bone or joint inflammation is the relief of pain and discomfort and the restoration of use of inflamed joints.

Certain enzymes play a role in causing inflammation. One of the features of inflammation is increased oxygenation of arachidonic acid, which is metabolized by two enzymic pathways—the cyclooxygenase (CO) and the 5-lipoxygenase (5-LO) pathways—leading to the production of prostaglandins and leukotrienes, respectively. Prostaglandins and leukotrienes are mediators of inflammation. Therapies designed to inhibit cyclooxygenase and/or lipoxygenase activity are therefore of great interest.

There are two forms of the cyclooxygenase enzyme: cyclooxygenase-1 (COX-1) and cyclooxygenase-2 (COX-2). The latter form, i.e., COX-2, appears to play a key role in inflammatory processes. Scientific studies suggest that inhibiting the COX-2 enzyme may be an effective way to reduce inflammation without the side effects associated with COX-1 inhibition. In addition, recent scientific studies also suggest that COX-2 inhibition may serve an important function in promoting normal cell growth in the colon, pancreas, breast tissue and other organ systems.

Drugs are being developed which are intended to selectively inhibit COX-2 with minimal effect on COX-1. However, despite the emphasis on COX-2 inhibition, these drugs appear to have serious side effects, e.g., a breakdown in digestive protective mucus and prevention of normal healing processes. For example, non-steroidal anti-inflammatory drugs (NSAIDS) can have a variety of toxic side effects such as, e.g., gastric erosion and adverse effects on kidneys and liver, and may inadequately regulate the cellular immune functions and secretions of various cytokines.

A major aspect of the mechanism of action of NSAIDS is generally thought to be the inhibition of cyclooxygenase, the enzyme responsible for the biosynthesis of some prostaglandins and certain related autacoids. This inhibition is dependent upon the drug reaching the cyclooxygenase enzyme, indicating that the mode of action is at the level of interaction with the enzyme protein itself. For example, acetaminophen can block the enzyme only in an environment that is low in peroxides, which may explain its poor anti-inflammatory activity since sites of inflammation usually contain high concentrations of peroxides generated by leukocytes. Aspirin acetylates a serine at or near the active site of cyclooxygenase, inhibiting the enzymatic activity. The most common unwanted side effect of NSAIDS and other aspirin-like drugs is a propensity to induce gastric or intestinal ulceration. More serious side effects, such as anemia from resultant blood loss, may also sometimes occur.

Glucocorticoids have the capacity to prevent or suppress the development of the manifestations of inflammation. They are also of immense value in treating diseases that result from undesirable immune reactions. The immunosuppressive and anti-inflammatory actions of the glucocorticoids are inextricably linked because they both result in large part from inhibition of specific functions of leukocytes, in particular, inhibition of lymphokines.

Natural ingredients, e.g., herbs, have been used to treat bone and joint inflammation. Compositions composed of natural ingredients and said to be useful in reducing inflammation are disclosed, e.g., in U.S. Pat. Nos. 6,264,995; 5,494,668; 5,683,698, 5,916,565, 5,888,514, 5,908,628; 5,788,971; 5,854,291; and 5,910,307, the entire contents and disclosures of which are hereby incorporated by reference herein.

Although some herbal compositions for reducing inflammation are known, it is desirable to provide alternative herbal compositions capable of reducing inflammation, particularly by inhibiting COX-2.

SUMMARY OF THE INVENTION

It is therefore an object of the present invention to provide an herbal composition capable of effectively reducing bone and joint inflammation by inhibiting COX-2.

It is a further object to provide an herbal composition capable of reducing inflammation while avoiding the side effects associated with traditional drug therapy.

It is yet another object to provide methods of reducing inflammation using an herbal composition having the characteristics set forth in the preceding objects.

Other objects and features of the present invention will be apparent from the following detailed description of the preferred embodiment.

According to a first broad aspect of the invention, the present invention provides an herbal composition for combating inflammation, comprising therapeutically effective amounts of Japanese knotweed, Devil's claw, grapeskin and syzygium.

According to a second broad aspect of the invention, the present invention provides an herbal composition for treating a cough and/or common cold, comprising therapeutically effective amounts of Japanese knotweed, lobelia, echinacea, slippery elm, Devil's claw, adhatoda, vitamin C, grapeskin, and syzygium.

According to a third broad aspect of the invention, the present invention provides an herbal composition for alleviating menstrual discomfort, comprising therapeutically effective amounts of Japanese knotweed, chaste tree berry, Mexican wild yam, dandelion, Devil's claw, grapeskin, and syzygium.

According to a fourth broad aspect of the invention, the present invention provides an herbal composition for soothing muscles and joints, comprising therapeutically effective amounts of Japanese knotweed, N-acetyl D-glucosamine, chondroitin sulfate, D-glucosamine hydrochloride, methylsulfonylmethane, Devil's claw, grapeskin, and syzygium.

Methods of using the herbal compositions of the present invention are also provided.

BRIEF DESCRIPTION OF THE DRAWINGS

The single Figure in the Drawings is a graph illustrating the relative inhibition of COX-1 and COX-2 by a composition of the present invention as compared with four commercially available compositions.

DETAILED DESCRIPTION OF THE PREFERRED EMBODIMENT

Figure 1:
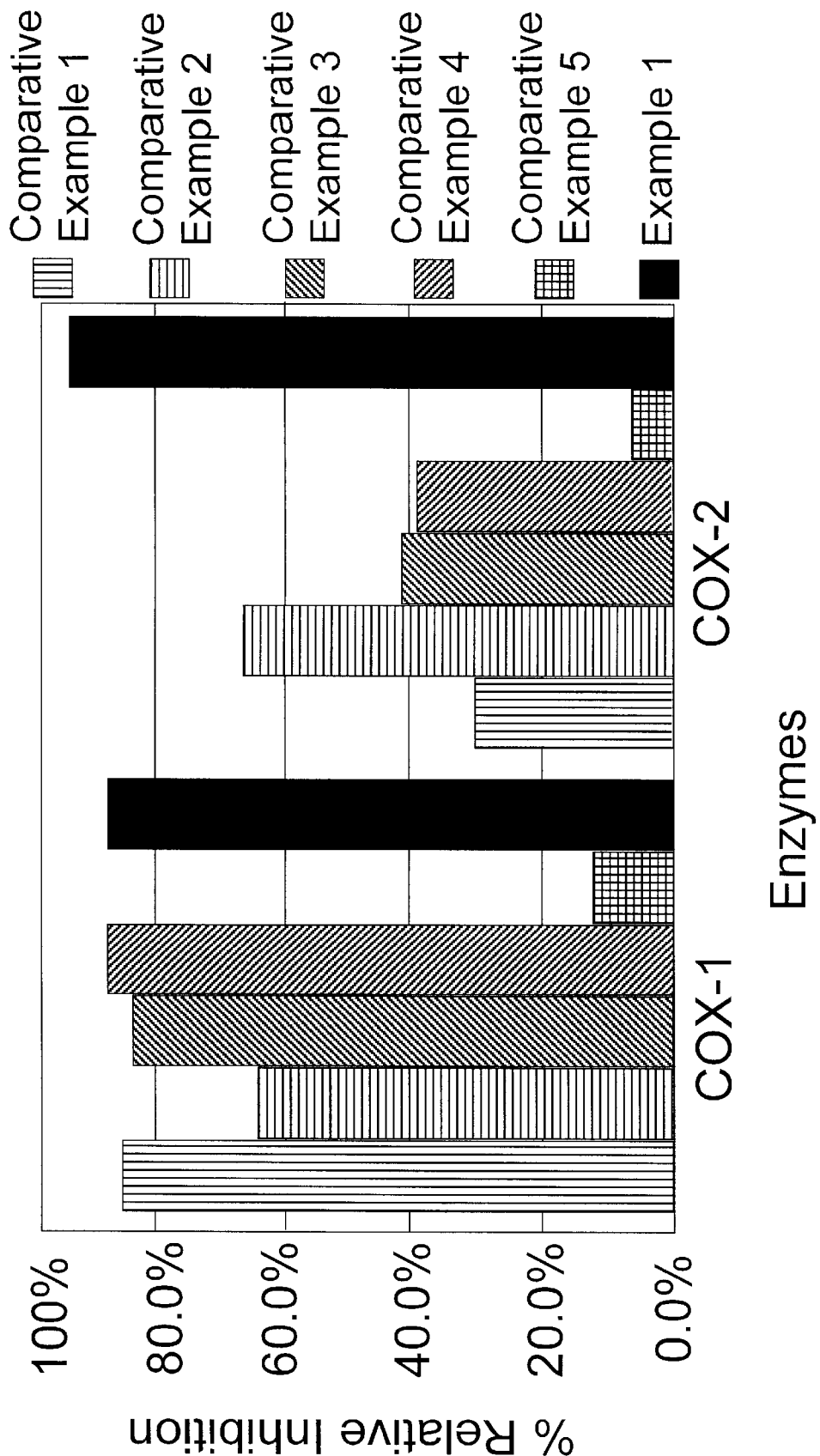

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "extract" means a concentrate of water-soluble and/or alcohol-soluble and/or other appropriate solvent-soluble plant components from the portion of the plant extracted and can be in liquid or powdered form.

For the purposes of the present invention, the term "dispensing apparatus" refers to a mechanical device that can hold units and dispense those units out through a controlled process.

For the purposes of the present invention, the term "therapeutically effective amount" means that amount of the whole herb (powdered or otherwise), extract or other component which, in conjunction with the amounts of the other whole herbs, herbal extracts or components present in the composition, promotes the ability of the overall composition to regulate the production of cyclooxygenase-2.

For the purposes of the present invention, the term "effective amount" means an amount sufficient to alleviate symptoms associated with inflammation.

Description

The present invention is based on the discovery that an herbal composition composed of specific herbs properly formulated or extracted and blended in correct proportions will safely and significantly inhibit COX-2, thereby reducing bone and joint inflammation and promoting normal cell growth. The herbs used in compositions of the present invention may be used in whole herb form, such as a powder, or in extracts or other suitable forms.

Thus, one aspect of the present invention is directed to an herbal composition composed of therapeutically effective amounts of Japanese knotweed, Devil's claw, grapeskin, and syzygium.

A further aspect of this invention is directed to a composition containing the herbal composition of this invention formulated together with a pharmaceutically acceptable carrier. In preferred embodiments, the composition is administered orally as a capsule (hard or soft gel) or tablet or topically as a cream. A still further aspect of this invention is directed to methods of using the herbal composition to alleviate symptoms associated with inflammation in persons afflicted with such symptoms.

Compositions of the invention may be useful for, but not limited to, the treatment of inflammation in a subject, and for treatment of other inflammation-associated disorders, such as, as an analgesic in the treatment of pain and headaches, or as an antipyretic for the treatment of fever. For example, combinations of the invention would be useful to treat arthritis, including but not limited to rheumatoid arthritis, spondyloarthopathies, gouty arthritis, osteoarthritis, systemic lupus erythematosus, juvenile arthritis, and/or prevention of conditions such as over-use arthritis and repetitive injury syndromes. Such compositions of the invention may be useful in the treatment of asthma, bronchitis, menstrual cramps, tendonitis, bursitis, and skin related conditions such as psoriasis, eczema, burns and dermatitis. Compositions of the invention also may be useful to treat gastrointestinal conditions such as inflammatory bowel disease, Crohn's disease, gastritis, irritable bowel syndrome and ulcerative colitis and for the prevention or treatment of cancer, such as colorectal cancer. Compositions of the invention may be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclerosis, sarcoidosis, nephritic syndrome, Behcet's syndrome, polymyositis, gingivitis, hypersensitivity, swelling occurring after injury, myocardial ischemia, and the like. The compositions may also be useful in the treatment of ophthalmic diseases, such as retinitis, retinopathies, conjunctivitis, uveitis, ocular photophobia, and of acute injury to the eye tissue. The compositions may also be useful in the treatment of pulmonary inflammation, such as that associated with viral infections, pleurisy, and cystic fibrosis. The compositions may also be useful for the treatment and/or prevention of certain central nervous system disorders such as cortical dementias including Alzheimer's disease. The compositions of the invention are useful as anti-inflammatory agents, such as for the treatment of arthritis, with the additional benefit of having significantly less harmful side effects. Besides being useful for human treatment, these compounds are also useful for treatment of mammals, including horses, dogs, cats, rats, mice, sheep, pigs, etc.

By inhibiting COX-2, an herbal composition of this invention also promotes healthy joint function and normal cell growth.

Compositions of the present invention may be used for a variety of ailments, such as to combat inflammation, treat a cough and/or common cold, alleviate symptoms associated with menstruation, and sooth muscles and joints.

According to an embodiment of the present invention, a composition for combating inflammation comprises Japanese knotweed, Devil's claw, syzygium, and grapeskin.

Japanese knotweed (*Polygonum cuspidatum*), in particular root extracts of Japanese knotweed, provides a source of resveratrol, which is a phytoestrogen that inhibits keratinocyte proliferation, increases keratinocyte differentiation, inhibits melanin production by the skin cells, and alleviates irritation or sting potentially associated with the use of alpha-hydroxy acids. Resveratrol is useful in improving the appearance of wrinkled, lined, dry, flaky, aged or photodamaged skin and improving skin thickness, elasticity, flexibility, radiance, glow and plumpness. Resveratrol is a well-known COX-1 inhibitor but that function is not being exactly reproduced by the present invention. Pure resveratrol (99%) is less effective than Japanese knotweed in inhibiting COX-2 but just as effective for COX-1. Thus, the COX-2 inhibitory activity of Japanese knotweed appears to be due to something other than the resveratrol component. Preferably, the Japanese knotweed utilized in the present invention provides at least 50% by weight total resveratrol having at least 10% by weight trans-resveratrol.

Devil's claw (*Harpagophytum procumbens*), in particular root and root extracts of Devil's claw, has been used as a tonic for the digestive system, arthritis, rheumatism, fever reduction, and for alleviating headaches.

Syzygium aromaticum has been used to relieve pain in teeth and relieve gastrointestinal tract disturbances and has been classified as an aromatic and carminative. Syzygium aromaticum also has antiseptic properties.

Suitable colorants for compositions of the present invention include grapeskin, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, other F.D. & C. dyes and natural coloring agents such as beet red powder, beta-carotene, carmine, turmeric, paprika, and other materials known to one of ordinary skill in the art.

In an embodiment of the present invention, a composition for combating inflammation comprises from about 10% to about 60%, preferably from about 20% to about 40%, and more preferably about 30%, by weight of Japanese knotweed, from about 5% to about 50%, preferably from about 30% to about 45%, and more preferably about 40%, by weight of Devil's claw, from about 5% to about 40%, preferably from about 7% to about 30%, and more preferably about 10%, by weight of syzygium and from about 5% to about 50%, preferably from about 10% to about 45%, and more preferably about 40%, by weight of grapeskin.

All percentages (%) contained herein are by weight unless otherwise indicated.

In an embodiment of the present invention, a composition for combating inflammation comprises from about 50 to about 100 mg Japanese knotweed, from about 75 to about 125 mg Devil's claw, from about 5 to about 40 mg syzygium and from about 25 to about 75 mg of grapeskin per dosage.

Dosages herein are exemplary for an individual having a body weight of approximately 75 kg. Modifications to the dosages may be made by one of ordinary skill in the art in light of the present specification.

In a preferred embodiment of the present invention, a composition for combating inflammation comprises 50 mg grapeskin, 75 mg Japanese knotweed, 100 mg Devil's claw and 25 mg syzygium per dosage.

Compositions of the present invention may, in addition, contain a therapeutically effective amount of at least one of the following: lobelia, echinacea, ma huang, slippery elm, elderberry, adhatoda, vitamin C, goldenseal, chaste tree berry, red raspberry, Mexican wild yam, dandelion, n-acetyl d-glucosamine, chondroitin sulfate, d-glucosamine hydrochloride and methylsulfonylmethane.

Alternative embodiments of the present invention may be used to treat a cough and/or common cold, alleviate symptoms associated with menstruation and/or sooth muscles and joints.

According to an embodiment of the present invention, a composition for treating a cough and/or a common cold comprises Japanese knotweed, Lobelia, Echinacea, slippery elm, Syzygium, adhatoda, vitamin C, goldenseal, grapeskin, and Devil's claw. In addition, a composition of the present invention may include ma huang.

Lobelia (*Lobelia inflata*), preferably the aerial extracts thereof, may be used as an anti-asthmatic, anti-spasmodic, expectorant, emetic, and/or nervine.

Echinacea (*Echinacea angustifolia*) and goldenseal (*Hydrastis Canadensis*) serve as immune boosting components. Echinacea and goldenseal may be used as the roots or root extracts.

Ma huang (Ephedra sinica), preferably the aerial extracts thereof, provide a source of ephedrine and is a mild energizing herb that suppresses appetite, promotes thermogenic metabolism, increases perspiration and stimulates the nervous system. It may be used for upper respiratory tract ailments and in natural cold remedies. For medicinal uses, the whole plant (in dried and powdered form) may be used, or the stems alone may be used. Preferably, the ma huang utilized in the present invention provides at least 8% by weight ephedra alkaloids.

Slippery elm (*Ulmus rubra*), preferably the bark thereof, is a fiber source that contains mucilage and also is helpful in easing intestinal evacuation and removing excess intestinal mucus.

Elderberry may be used as a flavorant. Exemplary flavorants include synthetic flavor oils and flavoring aromatics and/or natural oils, extracts from plants, leaves, flowers, fruits, etc. and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavorants include vanilla, citrus oil, including lemon, orange, grape, lime and grapefruit, and fruit essences, including apple, pear, peach, strawberry, red raspberry, cherry, plum, pineapple, apricot, etc. Other suitable flavorants are disclosed in U.S. Pat. Nos. 6,136,356 and 6,268,009 the entire contents and disclosures of which are hereby incorporated by reference herein.

Adhatoda (*Adhatoda vasica*) may be used in the management of allergic disorders and bronchial asthma. The alkaloids present in adhatoda possess respiratory stimulant activity. The leaves may be used as an expectorant, for example, in the manufacture of cough syrups and lozenges.

Vitamin C is an antioxidant. Antioxidants react with free radicals, such as hydroxy radicals, to protect certain biological systems. Vitamin C plays an integral role in the integrity of connective and structural tissues in the body.

In an embodiment of the present invention, a composition for treating a cough and/or common cold comprises from about 5% to about 10%, preferably about 8%, by weight of Japanese knotweed, from about 2% to about 8%, preferably about 5%, by weight of lobelia, from about 2% to about 8%, preferably about 5%, by weight of echinacea root extract, from about 15% to about 25%, preferably about 20% by weight of echinacea root, from about 2% to about 8%, preferably about 5% by weight of Devil's claw, from about 2% to about 8%, preferably about 5%, by weight of slippery elm, from about 1% to about 5%, preferably about 3%, by weight of syzygium, from about 5% to about 15%, preferably about 10%, by weight of adhatoda, from about 2% to about 8%, preferably about 5%, by weight of grapeskin, from about 5% to about 15%, preferably about 10%, by weight of vitamin C, and from about 1% to about 5%, preferably about 3%, by weight of goldenseal. In an embodiment of the present invention, the composition may include from about 5% to about 10%, preferably about 8%, by weight of ma huang. In addition, a composition of the present invention may include a suitable flavorant, such as elderberry or red raspberry.

In an embodiment of the present invention, a composition for treating a cough and/or common cold comprises from about 50 to about 100 mg Japanese knotweed, from about 25 to about 75 mg lobelia, from about 25 to about 75 mg echinacea root extract, from about 150 to about 250 mg echinacea root, from about 25 to about 75 mg Devil's claw, from about 25 to about 75 mg slippery elm, from about 10to about 40 mg syzygium, from about 50 to about 150 mg adhatoda, contain from about 25 to about 75 mg of grapeskin, from about 50 to about 150 mg Vitamin C, and from about 10 to about 40 mg goldenseal per dosage. In an embodiment of the present invention, the composition may include from about 50 to about 100 mg ma huang.

In a preferred embodiment of the present invention, a composition for treating a cough and/or common cold comprises 50 mg grapeskin, 57 mg Japanese knotweed, 50 mg Lobelia, 50 mg echinacea root extract, 200 mg echinacea root, 50 mg Devil's claw, 50 mg slippery elm, 25 mg syzygium, 100 mg elderberry, 100 mg adhatoda, 100 mg vitamin C and 25 mg goldenseal per dosage. In an embodiment of the present invention, the composition may include 57 mg ma huang.

According to an embodiment of the present invention, a composition for alleviating menstrual discomfort comprises Japanese knotweed, chaste tree berry, Mexican wild yam, dandelion, Devil's claw, grapeskin, and syzygium.

Chaste tree berry (*Vitex agnus-castus*) and Mexican wild yam (*Dioscorea composita*) are phytoestrogen-containing compounds. Preferably, the chaste tree berry, preferably the fruit extracts thereof, provides at least 0.5% agnuside.

The wild yam root and tuber have antispasmodic properties capable of easing menstrual cramps, as well as muscle relaxing, diuretic and anti-inflammatory properties. Key constituents of wild yam are starch and natural hormonal and steroidal compounds. Preferably, the wild yam provides at least 3.7% diosgenin.

Dandelion (*Taraxacum officinale*), preferably the root extracts thereof, may be used as a diuretic to reduce water retention and bloating. Dandelion is full of vitamin Bs and vitamin A. Both provide essential nutrition to every living cell in the body. Cells require vitamin B and A to provide health to all living tissue. It is also one of the best sources of potassium, replacing that which is flushed from the body when a diuretic is used. It thus makes an ideally balanced diuretic that may be used safely wherever such an action is needed, such as in cases of water retention due to cystitis and premenstrual syndrome.

In an embodiment of the present invention, a composition for alleviating menstrual discomfort comprises from about 5% to about 20%, preferably about 13%, by weight of Japanese knotweed, from about 3% to about 25%, preferably about 17%, by weight of chaste tree berry, from about 5% to about 20%, preferably about 13%, by weight of Mexican wild yam, from about 5% to about 15%, preferably about 9% by weight of dandelion, from about 10% to about 25%, preferably about 17% by weight of Devil's claw, from about 5% to about 25%, preferably about 17%, by weight grapeskin, and from about 1% to about 8%, preferably about 4%, by weight of syzygium. In addition, a composition of the present invention may include a suitable flavorant such as elderberry or red raspberry.

In an embodiment of the present invention, a composition for alleviating menstrual discomfort comprises from about 50 to about 100 mg Japanese knotweed, from about 15 to about 150 mg chaste tree berry, from about 50 to about 100 mg Mexican wild yam, from about 25 to about 57 mg dandelion, from about 50 to about 150 mg Devil's claw, from about 25 to about 57 mg of grapeskin, and from about 10 to about 40 mg syzygium per dosage.

In a preferred embodiment of the present invention, a composition for alleviating menstrual discomfort comprises 50 mg grapeskin, 57 mg Japanese knotweed, 100 mg chaste tree berry, 100 mg red raspberry, 57 mg Mexican wild yam, 50 mg dandelion, 100 mg Devil's claw, and 25 mg syzygium per dosage.

According to an embodiment of the present invention, a composition for soothing muscles and joints comprises Japanese knotweed, N-acetyl D-glucosamine, chondroitin sulfate, D-glucosamine hydrochloride, methylsulfonylmethane, Devil's claw, grapeskin, and syzygium.

N-acetyl-D-glucosamine is a rate-limiting factor in hyaluronic acid production by living cells. Hyaluronic acid, which is produced by all living skin of human beings, is a hydrating molecule, one gram being able to hydrate to a volume of 3 liters. When young skin cells are exposed after exfoliation, they produce larger quantities of hyaluronic acid which is a glycosaminoglycan which is composed of a chain of alternating, repeating, D-glucuronic acid and N-acetyl-D-glucosamine molecules. The topical application of glucosamine, or a readily metabolizable form of the glucosamine molecule, in particular N-acetyl-D-glucosamine, assists in the continued production of hyaluronic acid by increasing the available supply of a rate limiting substrate in the production of hyaluronic acid by skin cells. The molecules superoxide dismutase, cysteine, and vitamin E, stop the oxidative degradation of the hyaluronic acid present in the skin, thereby slowing the depletion of that hydrating substance.

The chondroitin sulfate family includes seven sub-types designated unsulfated chondroitin sulfate, oversulfated chondroitin sulfate and chondroitin sulfates A-E, which vary in the number and position of their sulfate functional groups. Additionally, chondroitin sulfate B, also referred to as dermatan sulfate, differs in that iduronic acid is the predominant residue in the alternative hexuronic acid position. Chondroitin sulfates A, B, and C are the predominant forms found in mammals and may be involved in the modulation of various biological activities including cell differentiation, adhesion, enzymatic pathways and hormone interactions. The chondroitin sulfate in compositions of the present invention is preferably in powder form.

D-glucosamine hydrochloride provides anti-inflammatory effects and may be used to treat inflammatory disorders of the gastrointestinal tract, including for example, ulcerative colitis and regional enteritis as evidenced by symptomatic remission, weight gain, decreased stool frequency, relief from abdominal cramping, shrinkage of intestinal polyps (as confirmed by sigmoidoscopy and biopsy) and decreased inflammation.

Methylsulfonylmethane has useful properties when applied to any animal tissue subject to undesired chemical bond formation including cross-linking. It may be used to beautify the complexion, to enhance scalp and hair, and generally to help make the body of the user more flexible and comfortable.

In an embodiment of the present invention, a composition for soothing muscles and joints comprises from about 5% to about 15%, preferably about 9%, by weight of Japanese knotweed, from about 1% to about 5%, preferably about 3%, by weight of N-acetyl D-glucosamine, from about 5% to about 20%, preferably about 11%, by weight of chondroitin sulfate, from about 25% to about 45%, preferably about 33% by weight of D-glucosamine hydrochloride, from about 15% to about 35%, preferably about 24% by weight of methylsulfonylmethane, and from about 5% to about 20%, preferably about 12%, by weight of Devil's claw, from about 5% to about 20%, preferably about 12%, by weight of grapeskin, and from about 2% to about 10%, preferably about 6% by weight of syzygium.

In an embodiment of the present invention, a composition for soothing muscles and joints comprises from about 50 to about 100 mg Japanese knotweed, from about 10 to about 40 mg N-acetyl D-glucosamine, from about 50 to about 150 mg chondroitin sulfate, from about 250 to about 350 mg D-glucosamine hydrochloride, from about 150 to about 250 mg methylsulfonylmethane, from about 50 to about 150 mg Devil's claw, from about 25 to about 57 mg of grapeskin, and from about 10 to about 40 mg syzygium per dosage.

In a preferred embodiment of the present invention, a composition for soothing muscles and joints comprises 50 mg grapeskin, 57 mg Japanese knotweed, 25 mg N-acetyl D-glucosamine, 100 mg chondroitin sulfate, 300 mg D-glucosamine hydrochloride, 200 mg methylsulfonylmethane, and 100 mg Devil's claw and 25 mg syzygium per dosage.

Extraction of these herbs may be carried out according to known extraction methods. Such methods are disclosed, e.g., in U.S. Pat. Nos. 6,264,995; 5,932,101; 5,908,628; 5,891,440; 5,874,084 and 5,120,558, the entire contents and disclosures of which are hereby incorporated by reference herein.

The herbal compositions of this invention may be prepared, for example, by individually washing, drying and grinding the herbs into fine powder, and then, if desired, extracting the ground herbs. The resulting ground herbs or extracts may then be mixed together in amounts that are physiologically acceptable to the patient. No special mixing means is required. The mixture of ground herbs or extracts may be encapsulated, tableted or formulated with a physiologically acceptable vehicle into unit dosages.

As stated previously herein, the herbal compositions of this invention may be administered in a variety of ways, including orally, topically (including opthalmically, vaginally, rectally, intranasally, and the like), and parenterally (e.g., by intravenous drip or by intraperitoneal, subcutaneous or intramuscular injection). Most preferably, the composition of this invention is administered orally or topically.

The orally administered embodiments of the herbal composition of this invention may be in any conventional form such as, e.g., capsules (hard or soft), tablets, elixirs, powders, granules, suspensions in water or non-aqueous media, sachets, as additives to food or beverages, or even may be made into a tea. Most preferably, the orally administered embodiment of the composition is in the form of a capsule (hard or soft gel) or tablet.

For preparing solid orally administered compositions such as capsules or tablets, the principal active ingredients may be mixed with a pharmaceutical carrier (e.g., conventional tableting ingredients such as cellulose, corn starch, lactose, sucrose, sorbitol, talc, stearic acid, magnesium stearate, dicalcium phosphate or gums) and other pharmaceutical diluents (e.g., water) to form a solid preformulation composition containing a substantially homogenous mixture of the composition of this invention, or a non-toxic pharmaceutically acceptable salt thereof. When referring to the preformulation compositions as substantially homogenous, it is meant that the active ingredients are dispersed reasonably evenly throughout the composition so that the composition may be readily subdivided into equally effective unit dosage froms such as capsules, pills and tablets. This solid preformulation composition can then be subdivided into unit dosage forms containing, for example, from 0.15 to 1.0 gram, of the active-ingredient composition.

Liquid preparations for oral administration may take the form of, for example, solutions, syrups or suspensions, or they may be presented as a dry product for reconstitution with water or other suitable vehicles before use. Such liquid preparations may be prepared by conventional means with pharmaceutically acceptable additives such as suspending agents (e.g., sorbitol syrup, methyl cellulose, or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The herbal composition of this invention may be combined with a physiologically acceptable oral vehicle into unit dosages. A unit dosage may comprise a therapeutically effective amount of each herbal extract for a single daily administration (e.g., orally), or it can be formulated into smaller quantities of each ingredient to provide for multiple doses in a day. A unit dosage will depend upon many factors including age, size, and condition of the individual being treated and the number of times the unit will be taken in a single day. In any event, the entire daily dosage will be that which is physiologically acceptable to an individual and may be administered daily over a prolonged period of time. In the present invention, normally between about 300 and 2000 mg of the active herb composition is preferably orally administered per day, with part of the total dose preferably taken at two or more different times during the day. When the orally administered composition is in the form of a capsule, the serving size of the composition is typically two capsules, with each capsule preferably containing from 0.15 to 1.0 gram of the active composition.

Formulations for topical administration may include but are not limited to lotions, ointments, gels, creams, suppositories, drops, liquids, sprays, and powders. Conventional pharmaceutical carriers; aqueous, powder or oily bases; thickeners and the like may be necessary or desirable. Most preferably, the topically administered embodiment of the composition of this invention may be in the form of a cream.

Formulations for parenteral administration may include but are not limited to sterile aqueous solutions that may also contain buffers, diluents and other suitable additives. The active ingredients may be formulated for parenteral administration by injection, which includes using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as stabilizing, suspending or dispersing agents. Alternatively, the active ingredients may be in powder form for reconstitution with a suitable vehicle, e.g., sterile pyrogert-free water, before use.

The exact proportion of the herbs or extracts used in the composition of this invention will depend on the concentration of active ingredients found naturally in each component. Using the guidance provided herein and a basic knowledge of drug preparation and pharmacology, one skilled in the art could easily adjust the proportions of the separate components of the composition so as to obtain a composition which has the therapeutic effects discussed herein.

The present invention is also directed to methods of reducing inflammation, involving orally, topically or parenterally administering an effective amount of the active-ingredient herbal composition of this invention to an individual in need of inflammation reduction. The effective amount will depend upon the severity of the symptoms and on the responsiveness of the patient to the herbal composition. Persons of ordinary skill in the art can easily determine optimum dosages, dosing methodologies, and repetition rates.

For topical use, the composition is preferably administered as a cream.

Suitable modes of parenteral administration include, e.g., intravenous drip; intraperitoneal, subcutaneous or intramuscular injection; and the like.

Oral administration is accomplished by ingesting the composition. As stated previously herein, the most preferred form of the orally administered composition of this invention is a soft gel capsule, which is preferably swallowed with water.

The composition identified above may further contain olive oil (certified organic) and/or yellow beeswax.

Soft gel capsules containing compositions of the present invention may further contain gelatin, vegetable glycerine, purified water and/or carob.

EXAMPLES

FIG. 1 is a graph illustrating the relative inhibition of COX-1 and COX-2 by a composition of the present invention as compared with five commercially available compositions.

The following publication: Bohlin L. et al. "Flavan-3-ols isolated from some medicinal plants inhibiting Cox-1 and Cox-2 catalyzed prostaglandin biosynthesis," Plant Med. 64, 1998, the entire contents and disclosure of which are hereby incorporated by reference herein, identifies some of the factors involved when considering the impact of the following data. The composition of the present invention appears to provide greater cyclooxygenase 2 (Cox 2) inhibitory activity relative to the comparative examples tested.

Example 1

In Example 1, 150 mg of the Nutra Mix™ composition of the present invention comprising 37.5% Japanese knotweed extract, 12.5% syzygium extract, 25% Devil's claw extract, and 25% grapeskin extract. The assay protocol is provided by the COX (ovine) Inhibitor Screening Assay kit (catalog # 560101) supplied by Cayman Chemical Company, Ann Arbor, MI, the entire contents and disclosure of which is hereby incorporated by reference herein. As is evident from the results, the composition of the present invention had a relatively high inhibitory effect on COX-2, as well as a high inhibitory effect on COX-1.

Comparative Example 1

In Comparative Example 1, the experimental protocol identified in Example 1 was utilized. Each SUPER FLEX® Back Formula tablet used in Comparative Example 1 contains 90 mg magnesium, 100 mg glucosamine, 400 mg MSM (methylsulfonylmethane), 100 mg boswellia serrata resin gum extract, 100 mg kava kava root, 33 mg ginger root, 15 mg turmeric (Curcuma longa extract), 5.4 mg Polygonum cuspidatum root extract. Other ingredients include microcrystalline cellulose, cellulose gum, magnesium stearate, stearic acid, and silicon dioxide. As is evident from the results, the composition of Comparative Example 1 had a relatively low inhibitory effect on COX-2, as well as a high inhibitory effect on COX-1.

Comparative Example 2

In Comparative Example 2, the experimental protocol identified in Example 1 was utilized. Each Zyflamend™ PM softgel capsule used in Comparative Example 2 contains 57 mg holy basil extract, 50 mg turmeric extract, 50 Mg Scutellaria baicalensis extract, 42.5 mg melissa extract, 37.5 mg ginger extract, 37.5 mg chamomile extract, 25 mg hops extract, and 10 mg valerain extract. Other ingredients include olive oil, beeswax, gelatin, glycerine, water, and carob. As is evident from the results, the composition of Comparative Example 2 had a relatively moderate inhibitory effect on COX-2, as well as a moderate inhibitory effect on COX-1.

Comparative Example 3

In Comparative Example 3, the experimental protocol identified in Example 1 was utilized. Each Zyflamend™ softgel capsule used in Comparative Example 3 contains 50 mg holy basil extract, 50 mg turmeric extract, 50 mg ginger extract, 50 mg green tea extract, 57 mg rosemary extract, 40 mg hu zhang (Polygonum cuspidatum) extract, 20 mg Chinese goldenthread extract, 20 mg oregano extract, and 20 mg Scutellaria baicalensis extract. Other ingredients include olive oil, beeswax, gelatin, glycerine, water, and carob. As is evident from the results, the composition of Comparative Example 3 had a relatively low inhibitory effect on COX-2, as well as a high inhibitory effect on COX-1.

Comparative Example 4

In Comparative Example 4, the experimental protocol identified in Example 1 was utilized. Each SUPER FLEX® Joint Formula tablet used in Comparative Example 4 contains 40 mg vitamin C, 6.7 mg manganese, 500 mg glucosamine, 333 mg MSM (methylsulfonylmethane), 100 mg Boswellia serrata resin gum extract, 33 mg ginger root, 15 mg turmeric (Curcuma longa extract), 5.4 mg Polygonum cuspidatum root extract. Other ingredients include microcrystalline cellulose, cellulose gum, magnesium stearate, stearic acid, and silicon dioxide. As is evident from the results, the composition of Comparative Example 4 had a relatively low inhibitory effect on COX-2, as well as a high inhibitory effect on COX-1.

Comparative Example 5

In Comparative Example 5, the experimental protocol identified in Example 1 was utilized. Each Nexrutine™ tablet used in Comparative Example 5 contains 165 mg calcium, 357 mg glucosamine sulfate, 150 mg chondroitin sulfate, and 125 mg philodendron amurense bark extract. Other ingredients include stearic acid, cellulose, cellulose gum, silica, magnesium stearate, hydroxypropyl methylcellulose, polyethylene glycol, and hydroxypropyl cellulose. As is evident from the results, the composition of Comparative Example 5 had a relatively low inhibitory effect on COX-2, as well as a low inhibitory effect on COX-1.

Inhibition of COX-2 is preferred. Comparative Examples 1, 2, 3, 4 and 5 show a high inhibitory effect on COX-1 with a significantly lower inhibitory effect on COX-2. COX-1 functions in pathways that are beneficial to the body, such as the promotion of a healthy stomach lining. Inhibition of COX-1 is therefore not preferred. As compared to Comparative Examples 1, 2, 3, 4 and 5, the composition of Example 1 shows a much larger ratio of COX-2 inhibition to COX-1 inhibition than that shown with the comparative compositions. Thus, compositions of the present invention provide benefits not produced by the presently available compositions.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An herbal composition for combating inflammation, comprising therapeutically effective amounts of Japanese knotweed, Devil's claw, grapeskin, and syzygium.

2. The composition of claim 1, comprising from about 10% to about 60% by weight of Japanese knotweed, from about 5% to about 50% by weight of Devil's claw, from about 5% to about 50% grapeskin and from about 5% to about 40% by weight of syzygium.

3. The composition of claim 2, comprising about 30% by weight of Japanese knotweed.

4. The composition of claim 2, comprising about 40% by weight of Devil's claw.

5. The composition of claim 2, comprising about 10% by weight of syzygium.

6. The composition of claim 2, comprising about 40% by weight of grapeskin.

7. The composition of claim 1, wherein the composition is an orally administrable composition.

8. The composition of claim 1, wherein the composition is a topically administrable composition.

9. The composition of claim 1, wherein the composition is a parenterally administrable composition.

10. An herbal composition for treating a cough and/or common cold, comprising therapeutically effective amounts of Japanese knotweed, lobelia, echinacea root, slippery elm, Devil's claw, grapeskin, adhatoda, vitamin C, and syzygium.

11. The composition of claim 10, further comprising ma huang.

12. The composition of claim 10, comprising:
   from about 5% to about 10% by weight of Japanese knotweed;
   from about 2% to about 8% by weight of lobelia;
   from about 15% to about 25% echinacea root;
   from about 2% to about 8% Devil's claw;
   from about 2% to about 8% grapeskin;
   from about 2% to about 8% slippery elm;
   from about 1% to about 5% syzygium;
   from about 5% to about 15% adhatoda;
   from about 5% to about 15% vitamin C; and
   from about 1% to about 5% goldenseal.

13. The composition of claim 12, further comprising from about 5% to about 10% ma huang.

14. The composition of claim 12, comprising about 8% by weight of Japanese knotweed.

15. The composition of claim 12, comprising about 5% by weight of lobelia.

16. The composition of claim 12, comprising about 20% by weight of echiniacea root.

17. The composition of claim 12, comprising about 5% by weight of Devil's claw.

18. The composition of claim 13, comprising about 8% by weight of ma huang.

19. The composition of claim 12, comprising about 5% by weight of slippery elm.

20. The composition of claim 12, comprising about 3% by weight of syzygium.

21. The composition of claim 12, comprising about 10% by weight of adhatoda.

22. The composition of claim 12, comprising about 30% by weight of vitamin C.

23. The composition of claim 12, comprising about 3% by weight of goldenseal.

24. The composition of claim 12, comprising about 5% by weight of Grapeskin.

25. The composition of claim 10, further comprising a flavorant.

26. The composition of claim 25, wherein said flavorant comprises elderberry.

27. The composition of claim 10, wherein the composition is an orally administrable composition.

28. The composition of claim 10, wherein the composition is a topically administrable composition.

29. The composition of claim 10, wherein the composition is a parenterally administrable composition.

30. An herbal composition for alleviating menstrual discomfort, comprising therapeutically effective amounts of Japanese knotweed, chaste tree berry, Mexican wild yam, dandelion, Devil's claw, grapeskin, and syzygium.

31. The composition of claim 30, comprising:
   from about 5% to about 20% by weight of Japanese knotweed;
   from about 10% to about 25% by weight of chaste tree berry;
   from about 5% to about 20% by weight of Mexican wild yam;
   from about 5% to about 15% dandelion;
   from about 10% to about 25% Grapeskin;
   from about 10% to about 25% Devil's claw; and
   from about 1% to about 8% Syzygium.

32. The composition of claim comprising about 13% by weight of Japanese knotweed.

33. The composition of claim 31, comprising about 17% by weight of chaste tree berry.

34. The composition of claim 31, comprising about 13% by weight of Mexican wild yam.

35. The composition of claim 31, comprising about 9% by weight of dandelion.

36. The composition of claim 31, comprising about 17% by weight of Devil's claw.

37. The composition of claim 31, comprising about 17% by weight of grapeskin.

38. The composition of claim 31, comprising about 4% by weight of syzygium.

39. The composition of claim 30, further comprising a flavorant.

40. The composition of claim 39, wherein said flavorant comprises red raspberry.

41. The composition of claim 30, wherein the composition is an orally administrable composition.

42. The composition of claim 32, wherein the composition is a topically administrable composition.

43. The composition of claim 30, wherein the composition is a parenterally administrable composition.

44. An herbal composition for soothing muscles and joints, comprising therapeutically effective amounts of Japanese knotweed, N-acetyl D-glucosamine, chondroitin sulfate, D-glucosamine hydrochloride, methylsulfonylmethane, syzygium, grapeskin, and Devil's claw.

45. The composition of claim 44, comprising:
   from about 5% to about 15% by weight of Japanese knotweed;
   from about 1% to about 5% by weight of N-acetyl D-glucosamine;
   from about 5% to about 20% by weight of chondroitin sulfate;
   from about 25% to about 45% D-glucosamine hydrochloride;

from about 15% to about 35% methylsulfonylmethane from about 5% to about 20% Devil's claw;

from about 5% to about 20% grapeskin; and from about 2% to about 10% syzygium.

46. The composition of claim 45, comprising about 9% by weight of Japanese knotweed.

47. The composition of claim 45, comprising about 3% by weight of N-acetyl D-glucosamine.

48. The composition of claim 45, comprising about 12% by weight of chondroitin sulfate.

49. The composition of claim 45, comprising about 35% by weight of D-glucosamine hydrochloride.

50. The composition of claim 45, comprising about 25% by weight of methylsulfonylmethane.

51. The composition of claim 45, comprising about 12% by weight of Devil's claw.

52. The composition of claim 45, comprising about 12% by weight of grapeskin.

53. The composition of claim 45, comprising about 6% by weight of syzygium.

54. The composition of claim 44, wherein the composition is an orally administrable composition.

55. The composition of claim 44, wherein the composition is a topically administrable composition.

56. The composition of claim 44, wherein the composition is a parenterally administrable composition.

57. A method for combating inflammation, comprising administering to an individual suffering from an inflammation an herbal composition comprising therapeutically effective amounts of Japanese knotweed, Devil's claw, grapeskin and syzygium.

58. The method of claim 57, wherein said composition comprises from about 10% to about 60% by weight of Japanese knotweed, from about 5% to about 50% by weight of Devil's claw, from about 5% to about 50% by weight of grapeskin, and from about 5% to about 40% by weight of syzygium.

59. A method for treating a cough and/or common cold, comprising administering to an individual suffering from a cough and/or common cold an herbal composition comprising therapeutically effective amounts of Japanese knotweed, lobelia, echinacea root, slippery elm, Devil's claw, adhatoda, vitamin C, grapeskin, and syzygium.

60. The method of claim 59, wherein said composition further comprises ma huang.

61. The method of claim 59, wherein said composition comprises:

from about 5% to about 10% by weight of Japanese knotweed;

from about 2% to about 8% by weight of lobelia;

from about 2% to about 8% by weight of echinacea root extract;

from about 15% to about 25% echinacea root;

from about 2% to about 8% Devil's claw;

from about 2% to about 8% grapeskin;

from about 2% to about 8% slippery elm;

from about 1% to about 5% syzygium;

from about 5% to about 15% adhatoda;

from about 5% to about 15% vitamin C; and from about 1% to about 5% goldenseal.

62. The method of claim 61, wherein said composition further comprises from about 5% to about 10% ma huang.

63. A method for alleviating menstrual discomfort, comprising administering to an individual suffering from menstrual discomfort an herbal composition comprising therapeutically effective amounts of Japanese knotweed, chaste tree berry, Mexican wild yam, dandelion, Devil's claw, grapeskin, and syzygium.

64. The method of claim 63 wherein said herbal composition comprises:

from about 5% to about 20% by weight of Japanese knotweed;

from about 10% to about 25% by weight of chaste tree berry;

from about 5% to about 20% by weight of Mexican wild yam;

from about 5% to about 15% dandelion;

from about 5% to about 25% grapeskin;

from about 10% to about 25% Devil's claw; and from about 1% to about 8% syzygium.

65. A method for soothing muscles and joints, comprising administering to an individual suffering from muscle and joint pain an herbal composition comprising therapeutically effective amounts of Japanese knotweed, N-acetyl D-glucosamine, chondroitin sulfate, D-glucosamine hydrochloride, methylsulfonylmethane, syzygium, grapeskin, and Devil's claw.

66. The method of claim 65, wherein said herbal composition comprises:

from about 5% to about 15% by weight of Japanese knotweed;

from about 1% to about 5% by weight of N-acetyl D-glucosamine;

from about 5% to about 20% by weight of chondroitin sulfate;

from about 25% to about 45% D-glucosamine hydrochloride;

from about 15% to about 35% methylsulfonylmethane;

from about 5% to about 20% Devil's claw;

from about 5% to about 20% grapeskin; and from about 2% to about 10% Syzygium.

* * * * *